(12) United States Patent
Waelti

(10) Patent No.: US 6,755,819 B1
(45) Date of Patent: Jun. 29, 2004

(54) METHOD AND DEVICE FOR THE PHOTOABLATION OF THE CORNEA WITH A LASER BEAM

(75) Inventor: Rudolf Waelti, Liebefeld (CH)

(73) Assignee: Haag-Streit AG, Koniz (CH)

( * ) Notice: Subject to any disclaimer, the term of this patent is extended or adjusted under 35 U.S.C. 154(b) by 0 days.

(21) Appl. No.: 10/070,559

(22) PCT Filed: Sep. 11, 2000

(86) PCT No.: PCT/CH00/00488

§ 371 (c)(1),
(2), (4) Date: Mar. 8, 2002

(87) PCT Pub. No.: WO01/19303

PCT Pub. Date: Mar. 22, 2001

(30) Foreign Application Priority Data

Sep. 10, 1999 (CH) .............................................. 1661/99

(51) Int. Cl.[7] .............................................. A61F 9/008
(52) U.S. Cl. .............................................. 606/5; 606/4
(58) Field of Search ........................ 351/160; 356/450, 356/451, 503, 511; 606/4–6

(56) References Cited

U.S. PATENT DOCUMENTS

| | | | | |
|---|---|---|---|---|
| 5,196,006 A | * | 3/1993 | Klopotek et al. | 606/32 |
| 5,490,849 A | * | 2/1996 | Smith | 606/5 |
| 5,493,109 A | * | 2/1996 | Wei et al. | |
| 5,720,894 A | * | 2/1998 | Neev et al. | |
| 5,858,454 A | * | 1/1999 | Kiryu et al. | 427/118 |
| 6,299,309 B1 | | 10/2001 | Ruiz | |
| 6,396,069 B1 | * | 5/2002 | MacPherson et al. | 250/559.22 |
| 6,454,761 B1 | * | 9/2002 | Freedman | 606/5 |

OTHER PUBLICATIONS

Böhnke, Matthias et al, Continuous Non–contact Corneal Pachymetry with a High Speed Reflectometer, Journal of Refractive Surgery, vol. 14, Mar./Apr. 1998.*

* cited by examiner

Primary Examiner—Roy D. Gibson
Assistant Examiner—Henry M. Johnson
(74) Attorney, Agent, or Firm—Birch, Stewart, Kolasch & Birch, LLP

(57) ABSTRACT

In a method for photoablation on the cornea with a laser beam with the aid of which a multiplicity of consecutive partial ablation operations are undertaken, the thickness of the cornea is determined with the aid of a measuring device co-operating with a Michelson interferometer before and after each partial ablation operation. By using the thickness values determined, the measuring device guides the laser beam, with intensity values appropriately adjusted by it, over the cornea in a controlled fashion so as not to undershoot a prescribed cornea thickness while complying with a prescribed cornea profile. The measuring device operates with a Michelson interferometer with a center wavelength of the measuring beam source in the region of 1,310 nm, and a monomode fiber for this wavelength in the reference arm such that the optical path length in air in the measuring arm can be acceptably compensated.

15 Claims, 13 Drawing Sheets

METHOD AND DEVICE FOR THE PHOTOABLATION OF THE CORNEA WITH A LASER BEAM

This application is the national phase under 35 U.S.C. § 371 of PCT International Application No. PCT/CH00/00488 which has an International filing date of Sep. 11, 2000, which designated the United States of America.

TECHNICAL FIELD

The invention relates to a method for the photoablation of the cornea with a laser beam, with the aid of which a multiplicity of consecutive partial ablation operations can be undertaken, and to a device with a laser radiation source for carrying out this method. The invention can be used, for one thing, to measure intraocular thicknesses and distances in the front eye section immediately before, during and immediately after surgical operations and treatments of the cornea. A photorefractive treatment can be controlled in real time depending on these measurement results. Control in real time leads to enhanced safety for the patient and to an improved accuracy of the photorefractive eye correction.

PRIOR ART

U.S. Pat. No. 5,493,109 discloses an ophthalmologic surgical microscope which operates with optical coherence tomography. Here, it was the surface shape of the cornea and the optical refractive power thereof that was determined.

SUMMARY OF THE INVENTION

OBJECT OF THE INVENTION

The object of the invention is to create a method and a device with the aid of which the cornea can be safely treated.

SUMMARY OF THE INVENTION

In terms of method, the object is achieved by virtue of the fact that the thickness of the cornea, and not only its surface shape and its optical refractive power are determined before and/or after each partial ablation operation with the aid of a measuring device co-operating with a Michelson interferometer. In addition, the position of the region envisaged for the ablation is determined and clearance for ablation is given only if the region is located within prescribed tolerance values. Defective ablation operations such as can occur owing to an eye movement, for example, are thereby excluded.

As a consequence of the determined thickness values of the cornea, the measurement device then guides the laser beam with corrected intensity in a controlled fashion over regions of the cornea that are still to be corrected in terms of thickness. The partial ablations are undertaken thereby in such a way that a prescribed cornea thickness is not undershot in conjunction with compliance of a prescribed cornea profile.

In terms of the device, provision is made for this purpose of a laser radiation source, a control device and a measuring device. The control device can have a beam deflecting unit with the aid of which the laser beam can be guided transversely over the cornea. The device according to the invention further has a measuring device with a Michelson interferometer with a center wavelength of the measuring radiation source in the region of 1,310 nm, and a monomode fiber for this wavelength in the reference arm such that the optical wavelength in air in the measuring arm, which is required for carrying out the measurement, can be compensated acceptably.

As is described below, various calibration curves relating to a determination of the optimum distance of the treatment site as well as inclination tolerances of the latter in relation to the treating laser beam axis are stored in the control device.

In particular, signal-distorting and signal-reducing consequences of the dispersion are minimized by the use of a measuring radiation source in the region of 1,310 nm with a bandwidth of up to approximately +/−100 nm. Specifically, if use is made of a radiation source with an arbitrarily prescribed center wavelength, there is generally a relatively long path in air of the order of magnitude of one meter in the measuring arm as a consequence of the structure prescribed by the operating microscope, the fundus camera or the laser. This path in air must be compensated in the reference arm either by a corresponding path in air or in another medium (preferably in a monomode fiber for space saving reasons), so that the required interference signals can be generated. If the path covered in air in the measuring arm is compensated in the reference arm by a corresponding distance in air, it is true that the dispersion produces only a slight signal distortion and signal reduction. However, in this case the reference arm can no longer be of compact design. If, however, the path covered in air in the measuring arm is compensated by a monomer fiber in the reference arm, relatively high signal distortion and signal reduction normally occur, because the dispersion properties differ in the reference arm and measuring arm. Very surprisingly, however, there is a wavelength region around 1,310 nm where this signal distortion and signal reduction are minimized such that the optical path of a measuring arm in air several meters long can be compensated by a path covered in the reference arm in a monomode fiber, without the interference signal being disturbed thereby. The interferometer can be of exceptionally compact and inexpensive design through the compensation of an optical path in a fiber.

In a preferred embodiment, the laser parameters such as the diameter on the cornea, intensity, power, energy and pulse duration of the laser radiation can also be controlled so that it is possible to take account of environmental influences on the result of the photorefraction such as air humidity and air temperature in the operation room, as well as patient-specific influences such as vaporization of chemicals stored in the operating room [for example (open) alcohol containers, (open) containers for cleaning agents], age, sex, composition of the patient's cornea and temperature of the patient's cornea. It would also be possible to take account of patient-specific data.

In order to render this possible, measurements have been made in previous research of the cornea thickness as a function of air humidity, air temperature in the operating room, age, sex, composition of the cornea and temperature of the cornea. The results of these measurements are then used to determine correction factors that feature in the control of the laser beam. An excellent result can then be achieved even given deviations from the normal conditions. It is even possible in the case of patients with irregular astigmatism, keratoconus or an irregular, corrugated cornea surface to undertake photorefractive corrections that reach the limit of approximately 20/5–20/8 (depending on pupil size) set by the laws of optical detraction.

Using the measuring arrangement described here it is possible for the first time to determine the front surface of the cornea, the rear surface of the cornea, the distance of the cornea from a reference site, the inclination of the cornea and thus the co-ordinates of the entire cornea in three-dimensional space online during the entire refractive surgical operation and this, moreover, in a contactless fashion.

BRIEF DESCRIPTION OF THE DRAWINGS

Examples of the device according to the invention and of the method according to the invention are explained below in more detail with the aid of the drawings, in which.

DESCRIPTION OF THE INVENTION

Figure 1:
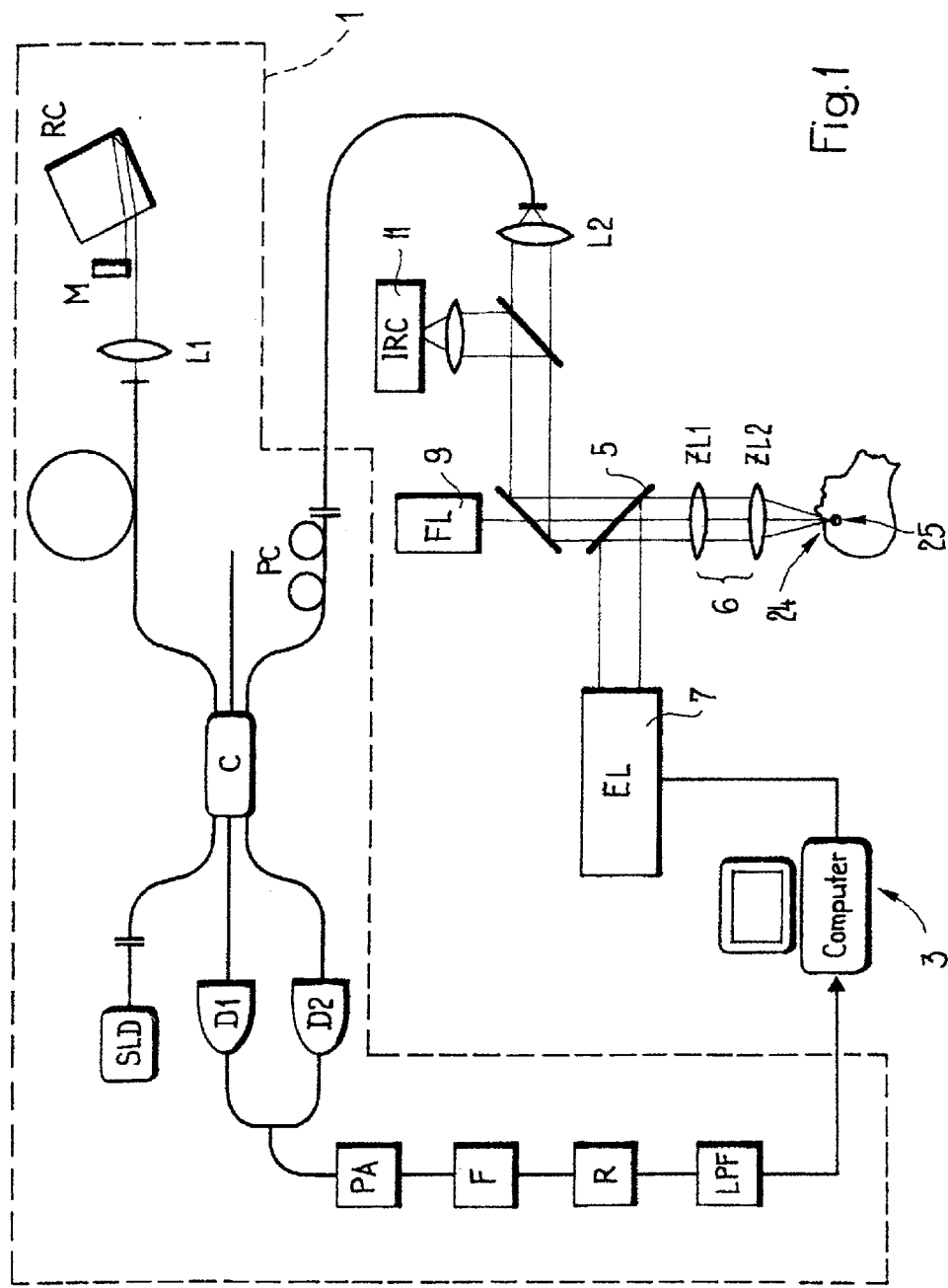
FIG. 1 shows a block diagram of the device according to the invention.

The invention described below is preferably used in eye treatment. The human eye is an exceptionally sensitive object which, in addition, is poorly fixed in its position. For this reason, together with the material ablation operation methods are specified for determining the position of the eye, the ablation that is undertaken with a laser being intended to go ahead only when the position of the eye region to be treated is optimal. Specifically, it can happen that the distance of the region to be treated from an optical focusing system for the laser radiation has changed. Again, the patient can have moved his eye slightly such that the axis of the treating radiation would no longer impinge perpendicularly. That is to say, material ablation and determination of position are interconnected. An ablation cannot be carried out if the location of the region is not satisfactory. The ablation operation is automatically blocked in the event of a deviation in position.

As already indicated above, in the case of a distance measurement the distance between the front surface of the cornea and a defined reference site is determined. The reference site can be a site prescribed starting from the therapeutic laser, or a site prescribed from the measuring unit. A site determined from the therapeutic laser is, for example, the co-ordinate of the optimal treatment site on the cornea. A site marked starting from the measuring unit is a defined position of the wavelength variator, used below, in the Michelson interferometer. This position can be specified by an "encoder".

A distance calibration is undertaken for each therapeutic unit before it is commissioned. If, for example a rotating cube is used in a Michelson interferometer for determining distance, as is described, for example, in WO 99/22198, the zero-degree position of the cube is a particularly excellent site. In this case, the surface, coated in a highly reflecting fashion, of the cube lies exactly perpendicular to the incident reference arm beam. The light retroreflected into the reference arm fiber in the case of this zero-degree position is measured by the electronic detecting system. The encoder is now adjusted such that it outputs an electric pulse precisely in the case of this zero-degree position. The temporal assignment of this reference pulse to a reflection pulse from the front surface of the cornea can be used to measure distances. Calibration is performed via an object reflecting at the optimal treatment site. This distance value is stored before the commissioning of the therapeutic unit and serves as reference value in subsequent treatment.

A glass plate adjusted at the optimal treatment site can be used as measurement object. An optimal site can be determined, for example, by using two pilot laser beams, in which case the glass plate should then be arranged at the site of the crossing beams.

Apart from the correct distance, it is also necessary to achieve a correct position of the region to be treated. The correct position has previously been checked with video cameras. The video image picked up was reproduced on a display screen and compared there with a prescribed indicated position. Although it was thereby possible to undertake position monitoring, it was impossible to detect tilting of the eye owing to a change in direction of view. It was therefore possible for decentered ablation patterns to be undesirably "fired at" in the case, for example, of a patient with fixation difficulties. Such instances of decentering can lead to inaccurate vision correction that may even require aftertreatment. It is possible by means of the arrangements described below to use the signal levels, measured with the aid of the measuring device, of the front and rear surfaces of the cornea to measure the inclination thereof online during refractive surgery and to adapt the ablation pattern if necessary with the aid of the measured data.

The levels of the electric detection signals from the front and rear surfaces are a function of the sensitivity of the measuring device, of the numeral aperture of the measuring beam, of the optical measuring light power impinging on the cornea, of the refractive indices of the cornea and of the anterior chamber of the eye, as well as of the inclination of the cornea relative to the measuring beam. The sensitivity of the measuring device, the numeral aperture of the measuring beam and the measuring light power incident on the cornea are known and constant. The refractive index of the cornea and of the anterior chamber of the eye fluctuates with different patients only in a small range. Consequently, the level of the measured signals is a function virtually only of the inclination of the cornea with reference to the measuring beam. Calibration measurements will therefore be undertaken in advance on various test subjects, and be stored as a function of the angle of inclination. When a patient undergoes ablation treatment, these calibration values can then be compared with the actual values and a current inclination can be determined therefrom. The treatment is interrupted if the angle of inclination determined in such a way is too large.

The block diagram, illustrated in FIG. 1, of the device according to the invention has a measuring device 1, described below in a plurality of variants, a control device 3 and a laser radiation source 7. The electronic control system 3 has a data memory cooperating with an evaluation unit, and a driver unit. The laser radiation from the radiation source 7 is directed onto a region to be treated on the cornea via a deflecting mirror 5 working also as a beam splitter and an optical system 6. The region to be treated can be marked by the beam of a fixing laser 9. The eye and the precise lateral position of the region to be treated are monitored, as already set forth above, by an infrared camera 11.

The laser radiation source 7 at the eye 25 is selected depending on the desired surgical techniques [PRK (photorefractive keratomy), PTK (phototherapeutic keratomy), LTK (laser thermokeratoplasty), LASIK (laser-assisted in-situ keratomileusis), LASEK (Laser Epithelial Keratomileusis)]. Thus, an excimer laser will be used for the ablation of parts of the cornea 24, and a holmium laser for heating the cornea. LASEK is based on the detachment of an epithelium or an epithelial flap by an alcoholic solution. The detached epithelium is rolled away to the side with a sort of spatula. The laser then fires directly onto the open stroma of the cornea and ablates it down to the desired shape. Thereafter, the epithelium or the epithelial flap is rolled back to its earlier position. A soft contact lens is mounted and worn for a few days so that the repositioned epithelium or the epithelial flap does not shift.

Figure 2:
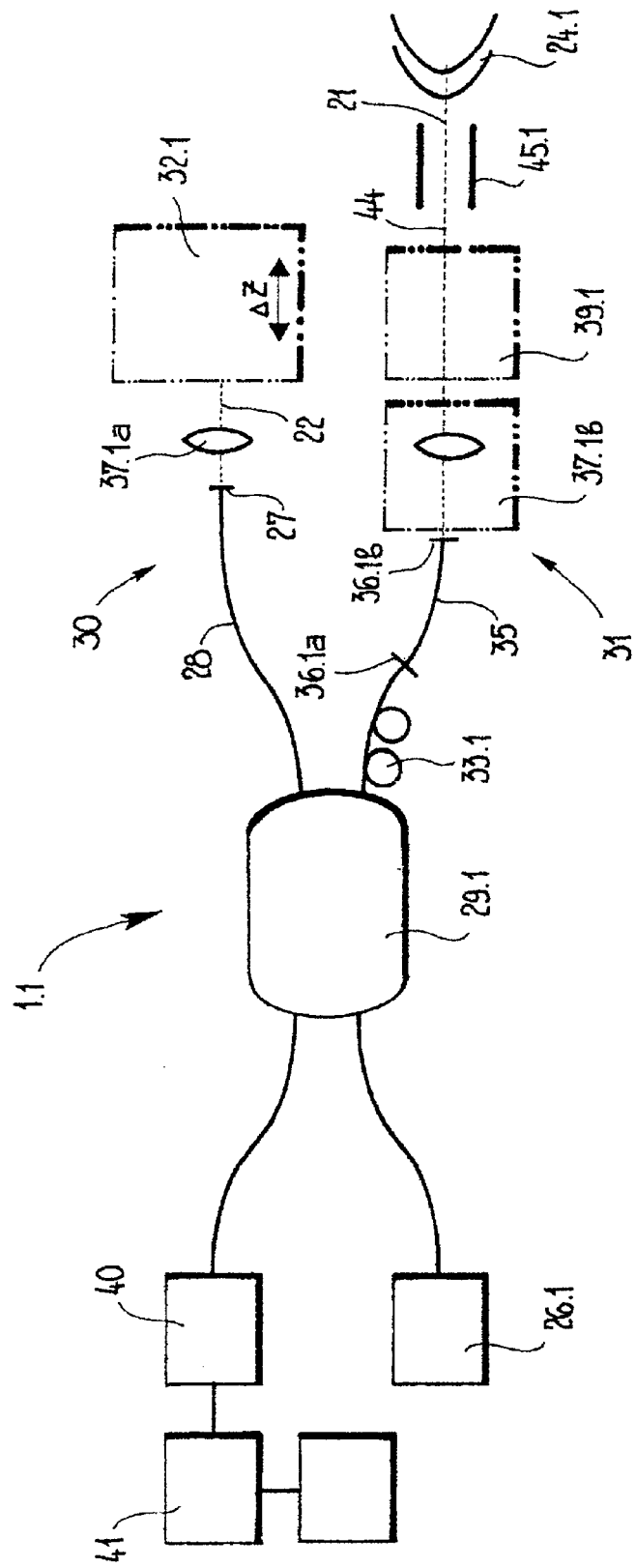
FIG. 2 shows a measuring device of the device illustrated in FIG. 1 with a 2×2 fiber coupler.

An exemplary measuring device 1 is illustrated in FIG. 2. The measuring device 1 is designed along the lines of a Michelson interferometer. It has a radiation source 26.1, preferably with a short coherence length (typically 15 $\mu$m to 30 $\mu$m) whose radiation is coupled into a 2×2 fiber coupler 29.1. The coherence length is short by comparison with the thickness to be determined for the cornea. A fiber coupler 29.1 has two inputs and two outputs. It splits the radiation into two portions. One portion of the radiation is shone into a reference arm 30 with an optical coupling system 37.1$a$, illustrated in a simplified way as a lens, and an optical wavelength variator 32.1. The optical wavelength variator 32.1 causes a temporal change in the optical wavelength in the reference arm 30 by a distance AZ. The radiation emerging from the end 27 of one radiation conductor 28 exiting from the fiber coupler 29.1 is converted into a parallel free-space beam 22 by the optical coupling system 37.1$a$. The measuring arm 31 further has a polarization controller 33.1, a monomode fiber 35 with two fiber plugs 36.1$a$ and 36.1$b$, an optical coupling system 37.1$b$ and an optical unit 39.1 that is designed specifically for a prescribed treatment purpose using the laser radiation source 7 (therapeutic laser). The beam deflecting unit 19 illustrated in FIG. 1 can belong to the optical unit 39.1. The optical coupling system 37.1$b$, which is illustrated in a simplified way as the deflecting mirror 5 which works also as a beam splitter in FIG. 1, can consist, for example, of a lens system and a beam splitter. The polarization monitor 33.1 is required in order, in particular, to match the direction of polarization of the radiation reflected by the measurement object 24, here the cornea 24.1 of the human eye 25, to the direction of polarization of the radiation reflected in the wavelength variator 32.1, this being done in such a way that an interference signal generated by a superimposition of radiation in the fiber coupler 29.1 reaches maximum intensity. The polarization controller 33.1 can also be arranged in the reference arm 30 instead of in the measuring arm 31. The radiation reflected by the reference arm 30 in the wavelength variator 32.1 and by the measurement object 24.1 is superimposed in the fiber coupler 29.1, and a partial radiation component is guided to a photodiode 40. The electric signal is led from the photodiode 40 to an electronic signal processing unit 41. The unit 41 consists, for example, of an electronic amplifier stage, an electronic filtering system, a rectifier and a lowpass filter for generating an envelope signal. The data and values determined by the unit 41 are then relayed to the evaluation unit 111 located in FIGS. 2 and 9 and from there to the data memory 13, and stored for further processing.

As already indicated above, a transverse optical beam deflecting system (not illustrated) can optionally be installed in the optical coupling system 37.1$b$. It is possible to use this beam deflecting system to detect both the topography and the tomography of the cornea 24 (for example cornea thickness at a plurality of transverse points), and then display them on a display screen. This beam deflection system has the effect of deflecting the measuring beam from the center position on the cornea 24. Consequently, the cornea thickness can be measured at the points adjacent to the center in the case of small deflections of the beam deflecting system. An interference signal that is as good as possible in the zone of maximum ablation is thereby obtained even in the case of patients with high astigmatism or keratoconus. The cornea thickness can be measured at peripheral points of the cornea in the case of larger deflections of the beam deflecting system.

Examples of deflecting systems 19 are:
1) two moveable mirrors for two transverse directions of deflection
2) a single moveable mirror that can be moved in such a way that both transverse directions of deflection can thereby be executed. [Advantages compared to 1) are saving of space and fewer components.]
3) A lens that can be moved transversely (horizontally and vertically). [Advantages as compared with 2): saving of space and fewer components.]

In order always to be able to cause the transversely deflected free measuring beam 44 to impinge approximately perpendicularly even on the peripheral region of the cornea 24, the measuring beam 44 can, for example, be deflected directly in front of the patient's eye with the aid of a specially shaped mirror 45.1. As indicated in FIG. 2, this specially shaped mirror 45.1 can be, for example, an aluminized hollow cylinder 45.1 (with an open end at left and right), or another hollow member with two openings, which is positioned in front of the patient's eye 25. Such a mirror 45.4 is explained below with the aid of FIG. 5.

Figure 3:
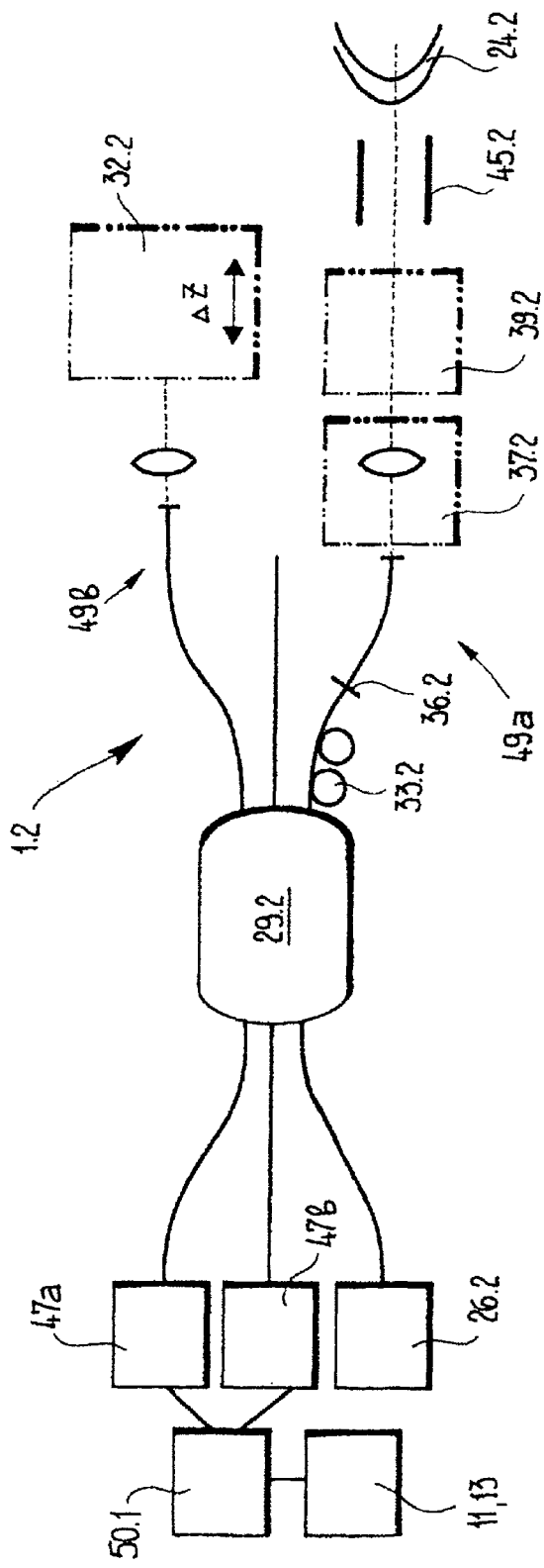
FIG. 3 shows a variant of the measuring device illustrated in FIG. 2, with a 3×3 fiber coupler.

FIG. 3 shows a measuring device 1.2 analogous to FIG. 2. Only a 3×3 fiber coupler 29.2 is present instead of the fiber coupler 29.1 of FIG. 2, and two photodiodes 47$a$ and 47$b$ are present instead of the one photodiode 40. The fiber coupler 29.2 is a 3×3 fiber coupler with three inputs and three outputs. The interference signal of the radiation reflected in the measuring and reference arms 49$a$ and 49$b$ there is now led with the aid of the 3×3 fiber coupler 29.2 to two photodiodes 47$a$ and 47$b$. By comparison with only one photodiode 40 as in FIG. 2, a substantial reduction in noise is possible (for example intensity noise of the radiation source) by an appropriate evaluation of the electronic signals of the two photodiodes 47$a$ and 47$b$ in a signal processing unit 50.1 designed by analogy with the signal processing unit 41.

Figure 4:
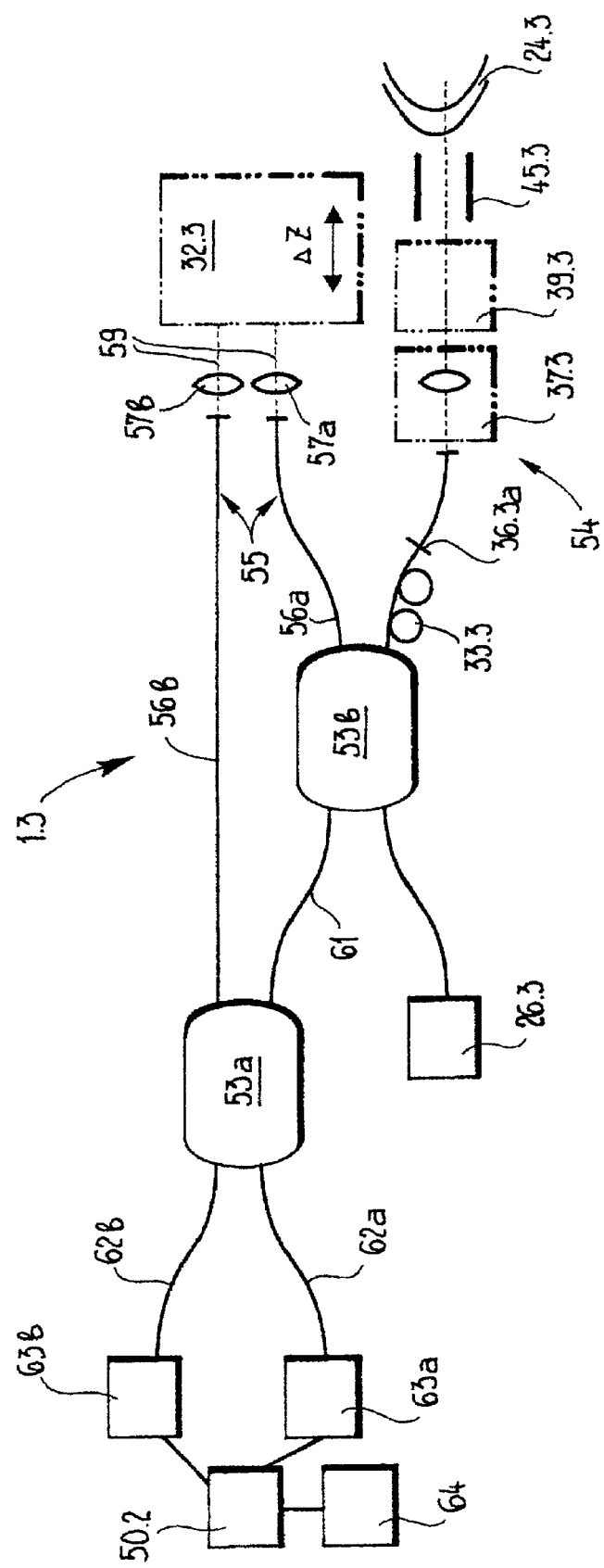
FIG. 4 shows a variant of the measuring device illustrated in FIG. 2, with two 2×2 fiber couplers.

Illustrated in FIG. 4 is a measuring device 1.3 that has two 2×2 fiber couplers 53$a$ and 53$b$. A larger noise component can be eliminated by comparison with the measuring devices 1.1 and 1.2 with the aid of this measuring device 1.3.

The measuring radiation goes from a radiation source 26.3, designed by analogy with the radiation sources 26.1 and 26.2 to the fiber coupler 53b, and is split here into the measuring arm 54 and a reference arm 55. The reference arm 55 has the path length variator 32.3, the two radiation conductors 56a and 56b, and the two collimation units 57a and 57b. By contrast with the measuring devices 1.1 and 1.2 of FIGS. 2 and 3, the beam 59 is now not fed back again into the same radiation conductor 56a, but is coupled after being focused by the collimator unit 57b into a radiation conductor 56b that is connected to the fiber coupler 53a.

The radiation in the measuring arm 54 which, by analogy with the configurations in the measuring arrangements 1.1 and 1.2, likewise has a polarization controller 33.3, an optical coupling system 37.3, an optical unit 39.3 and a specially designed mirror 45.3, is likewise reflected at a cornea 24.3 to be measured and then runs back in the measuring arm 54 as far as a fiber coupler 53b. Depending on the method used, the radiation then passes through a radiation conductor 61 to the fiber coupler 53a. An interfering superimposition of the incoming radiations of the radiation conductors 56b and 61 is then performed in the fiber coupler 53a. The interfering radiation is guided once via a radiation conductor 62a onto a radiation detection unit 63a, and once more onto a radiation detection unit 63b via a radiation conductor 62b. The electric detection signals of the two units 63a and 63b are led to a signal processing unit 50.2 of analogous design to the signal processing unit 50.1 and processed thereby. Further processing in relation to one of the uses named below is then performed with the aid of an evaluation unit 64 that is connected to the unit 50.2 by signal and preferably includes the required data memory.

The advantage of the circuit shown in FIG. 4 consists in that the noise component (for example intensity noise of the radiation source 26.3) can be diminished by using the two radiation detection units 63a and 63b. The two radiation detection units 63a and 63b are connected in antiparallel so that that portion of the radiation flux impinging on one unit that cannot be used for the evaluation generates a positive electric current signal, while the portion of the radiation flux impinging on the other units that cannot be used for the evaluation generates a negative electronic current signal. The two current signals are combined and thereby cancel each other. That portion (that is to say the interference signal, here a temporally limited sine-wave sequence) of the radiation impinging on one radiation detection unit that can be used for the evaluation has a phase shift of $\pi$ relative to the interference signal that impinges on the other radiation detection unit. A sine-wave sequence is produced again if two temporally limited sine-wave sequences are phase-shifted and subtracted from one another (as a function of the antiparallel connection of the two radiation detection units 63a and 63b). By contrast with the noise, in the case of the interference signal this antiparallel connection does not cause extinction. It may be mentioned in addition that this principle can also be used in the case of the photodiodes 47a and 47b in the arrangement illustrated in FIG. 3, although here phases of the interference signals are shifted not by $\pi$ but by $\frac{2}{3}\pi$ relative to one another because of the use of a 3×3 fiber coupler 29.2.

Figure 5:
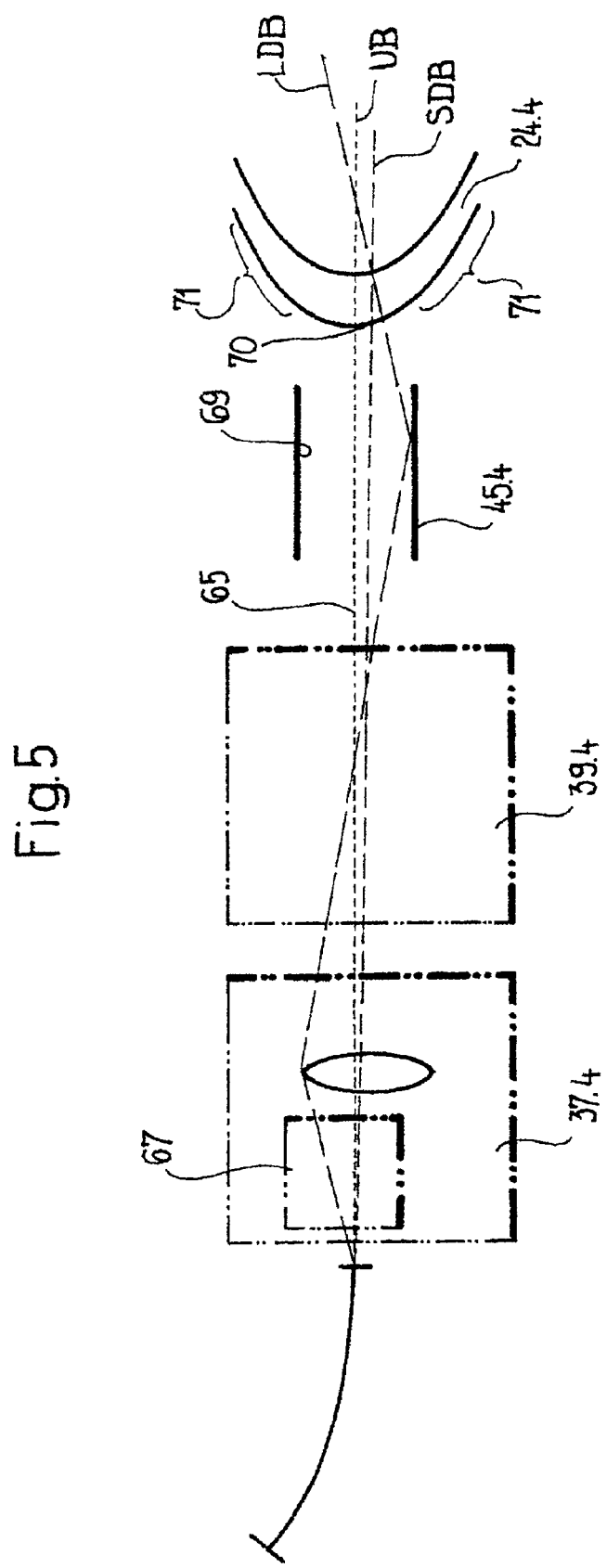
FIG. 5 shows a beam path of the measuring beam, in the case of which the latter always strikes the measurement object approximately perpendicularly.

FIG. 5 shows the beam path of the measuring beam for a non-deflected, free beam UB (dotted) on the optical axis 65, a beam SDB (dashed) deflected slightly from the optical axis 65 by a beam deflecting unit 67, and a beam LDB (dashed and dotted) deflected far from the optical axis 65 by means of the beam deflecting unit 67 of an optical coupling system 37.4 designed by analogy with the coupling units 37.1 to 37.3. A mirror 45.4 with a design analogous to mirrors 45.1 to 45.3 and whose reflecting surface 69 is arranged parallel to the optical axis 65 deflects the beam LDB here onto the cornea 24.4 such that the beam LDB impinges approximately perpendicularly on the peripheral cornea 24.4 so as to render possible even peripheral thickness measurements of the cornea 24.4. The measuring beam SDB that is deflected only slightly from the optical axis 65 by the beam deflecting unit 67 does not impinge on the mirror 45.4. It is not necessary for the beam SDB to impinge on the mirror 45.4, because the beam SDB still impinges sufficiently close to the central point 70 (up to approximately 1 mm) of the cornea 24.4 such that the deviation from the perpendicular incidence is still sufficiently small to detect an interference signal. The surface curvature needs to be corrected by "kinking" the beam LDB with the aid of the mirror 45.4 only for peripheral regions 71 of the cornea 24.4 in the case of which the curvature thereof has already become noticeable.

Figure 6:
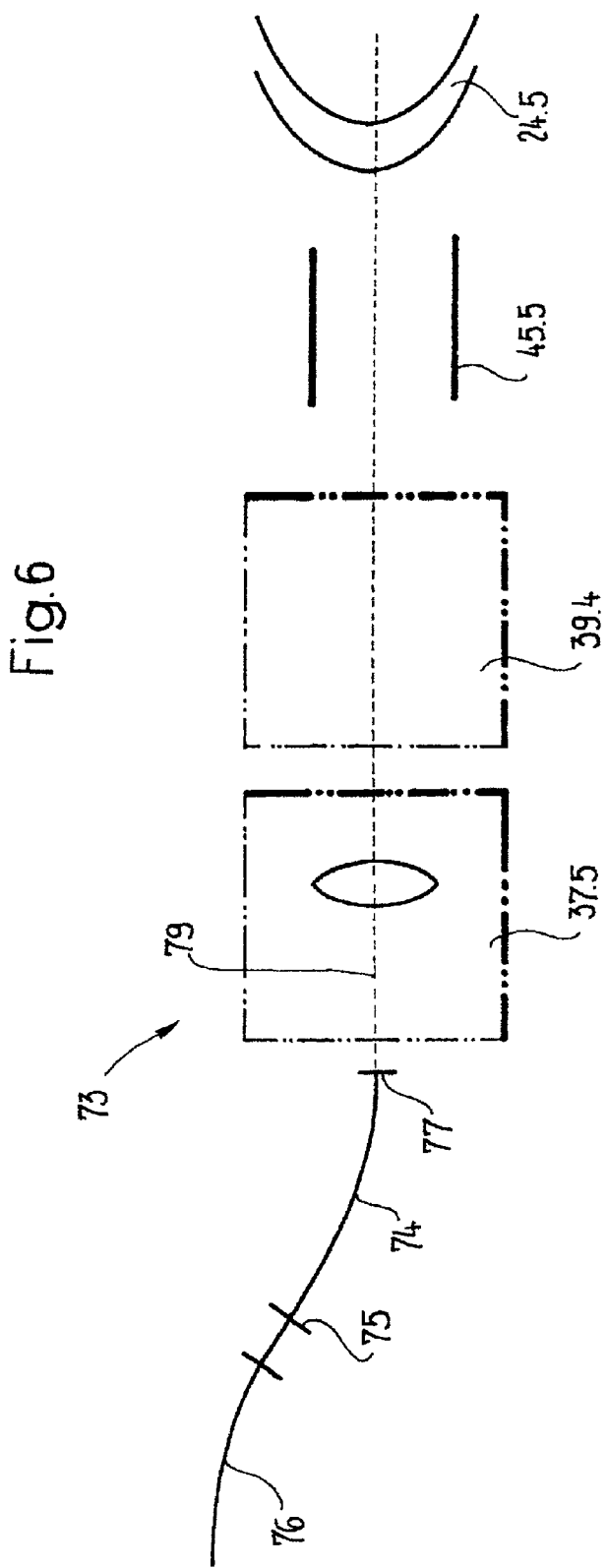
FIG. 6 shows an exemplary arrangement of the measuring arm with a polarization-maintaining fiber.

FIG. 6 shows an exemplary arrangement of a measuring arm 73 which can be used instead of the measuring arms 31, 49a and 54. The measuring arm 73 has a polarization-maintaining fiber 74 that is connected with the aid of a plug 75 for this polarization-maintaining fiber 74 to a fiber 76 leading to one of the fiber couplers 29.1, 29.2 or 53b. It is also possible to use a plug for fibers that do not maintain polarization. By contrast with the "normal" monomode fiber 76, the position of the polarization-maintaining fiber 74 can be changed without thereby having an effect on the interference signal generated. It is possible to use an adjustable angular position of the plug 75 to match the direction of polarization of the free-space beam 79, emerging from the fiber end 77 of the fiber 74, to the direction of polarization of the radiation in the reference arm 30, 49b or 56b. As a consequence of the configuration, sketched in FIG. 6, of the measuring arm 73, it is possible to dispense with the polarization controllers 33.1, 33.2 or 33.3 necessary in FIGS. 2 to 4 and 9 in the measuring arms 31, 49a or 54 there. The measuring arm, and thus the entire measuring devices can be of smaller and less expensive design owing to the emission of the polarization controllers 33.1, 33.2 or 33.3.

Figure 7:
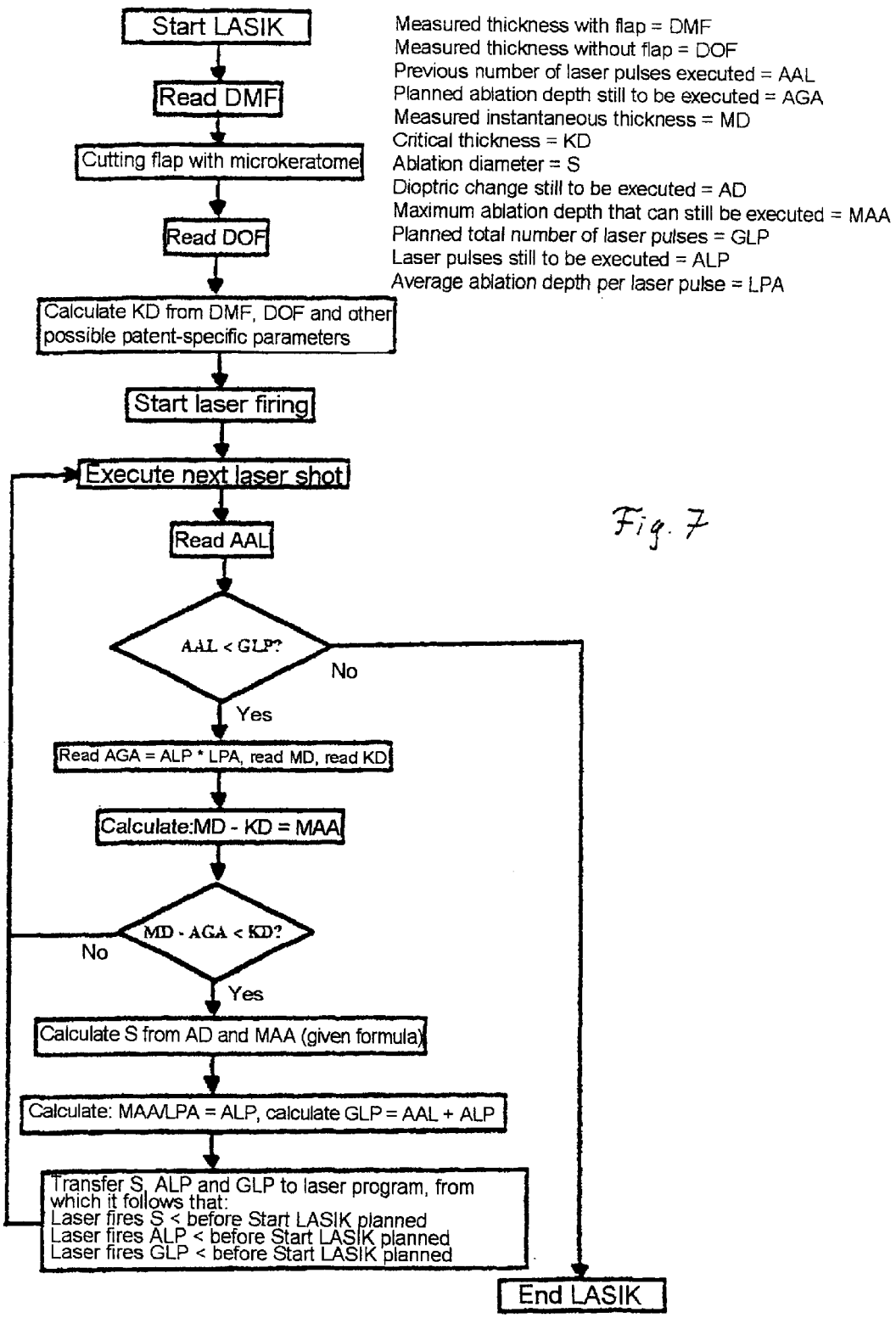
FIG. 7 shows a flowchart that illustrates a method in the case of ablation for LASIK.

FIG. 7 shows a flowchart that illustrates a method in the case of ablation for LASIK [Laser-assisted in-situ Keratomileusis]. The aim of LASIK as of the other "refractive operations" such as, for example, PRK or LASEK, is to correct vision defects, such as short sightedness or far sightedness, in such a way that it is possible to dispense with spectacles or contact lenses. It shows how and when the cornea thickness measurements are used in order to control the "LASIK operation". This flowchart holds both for myopia and for hyperopia LASIK. The sole difference between the methods for the myopia and hyperopia LASIKs consist in that a different formula is used to calculate the ablation diameter as a function of the dioptric change. LASIK is a refractive operation in the case of which a microkeratome is used to cut a cornea flap with a thickness of approximately 150 µm. This flap stays joined at one end to the remainder of the cornea. This flap is then folded over. Laser pulses are then fired onto the stroma, thus exposed, of the cornea until the desired ablation is achieved. After inclusion of the ablation, the cornea flap is folded back again and placed at the original site.

In a first method step, the thickness $d_{mF}$ of the cornea with flap is determined with the aid of one of the above described measuring devices 1.1, 1.2 or 1.3. The path variation length $\Delta Z$ of the path length variators 32.1, 32.2 or 32.3 must be at least as large as the thickness to be measured for the cornea. Interference always occurs whenever the path lengths are equal in the reference arm and in the measuring arm. Since the path length in the reference arm is changed with the aid of the path length variators 32.1, 32.2 or 32.3, an interference signal is respectively ascertained by the relevant evaluation unit 11; 41, 50.1 and 50.2 after evaluation of the signals detected by the detector 40 or by the two detectors 47a and 47b or 63a and 63b when the path lengths in the measuring arm up to the front side of the cornea and up to the rear side thereof are of the same magnitude as the path lengths in the reference arm. The two interferences then yield the thickness DMF of the cornea 24.1 with flap by subtraction. This thickness DMF is stored in a data memory belonging to the evaluation unit.

In a next method step, the flap is cut free and folded back. A renewed thickness measurement DOF without flap is now carried out by analogy with the above description. The thickness value DOF determined thereby is likewise stored. The critical thickness KD is now determined by the evaluation unit while taking account of the cornea thickness with and without flap DMF and DOF as well as any possible further patient-specific parameters. The critical thickness KD is a thickness value of the cornea that may not be undershot for reasons of stability, inter alia. A first laser pulse is now undertaken by the first partial ablation of the cornea, and the instantaneous thickness MD of the cornea is subsequently determined using the measuring method explained above. A difference between the thickness value DOF of the cornea without flap and this instantaneous thickness value MD gives a thickness ablation value $d_{ab}$ per laser pulse. Since the thickness ablation value $d_{ab}$ per laser pulse is now known, it can be acceptably determined how many laser pulses are required for the ablation of the cornea for a prescribed residual cornea thickness $d_{rest}$. The number of required laser pulses is determined in such a way that a prescribed critical cornea thickness KD is not undershot. A thickness measurement with flap has been undertaken in advance. A critical residual thickness of the cornea can depend on its initial thickness. This critical residual thickness KD is preferably determined in accordance with the following formula:

$$KD = a \cdot DMF - b,$$

DMF being the initial thickness of the cornea (that is to say before the first intervention at the cornea). The variables a and b are determined by the applicant. Given as standard values possibly requiring correction are a=0.58 and b=30 µm.

Figure 8:
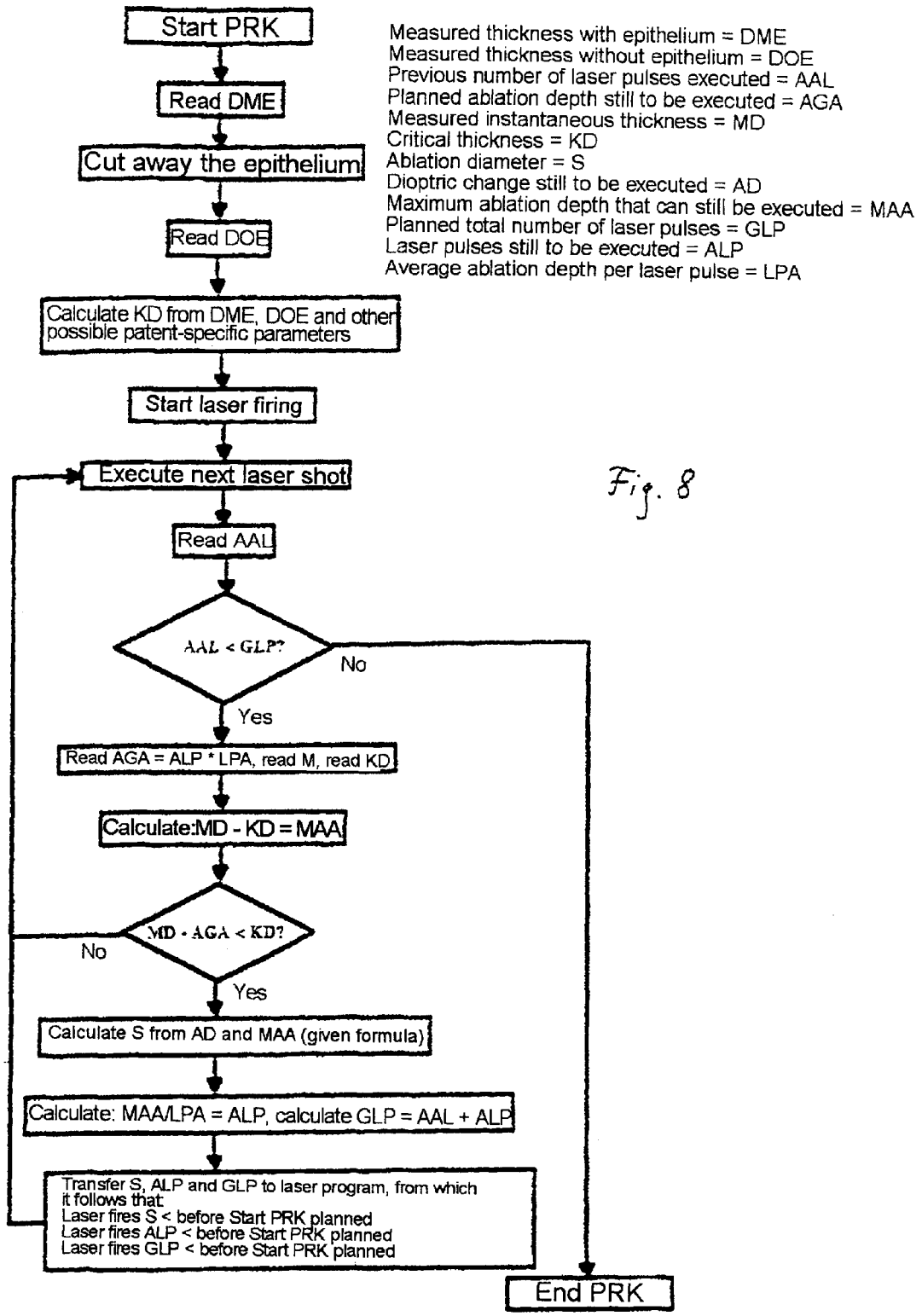
FIG. 8 shows a flowchart that illustrates a method in the case of ablation for PRK (photorefractive keratectomy)

Instead of cutting the flap and folding it away, the epithelium can also be scraped away. In this case, the thickness of the cornea is measured once with the epithelium and once after removal of the epithelium. In the method sequence set forth, the value DMF is then replaced by the thickness value with epithelium DME, and DOF by that without epithelium DOE. FIG. 8 shows the flowchart belonging hereto, which illustrates a method in the case of the ablation for PRK [photorefractive Keratectometry]. It shows how and when the cornea thickness measurements are used in order to control the PRK operation. This flowchart holds both for myopic and for hyperopic corrections. The sole difference between the method for the myopic and hyperopic PRK consists in that a different formula must be used to calculate the ablation diameter as a function of the dioptric change.

Figure 9:
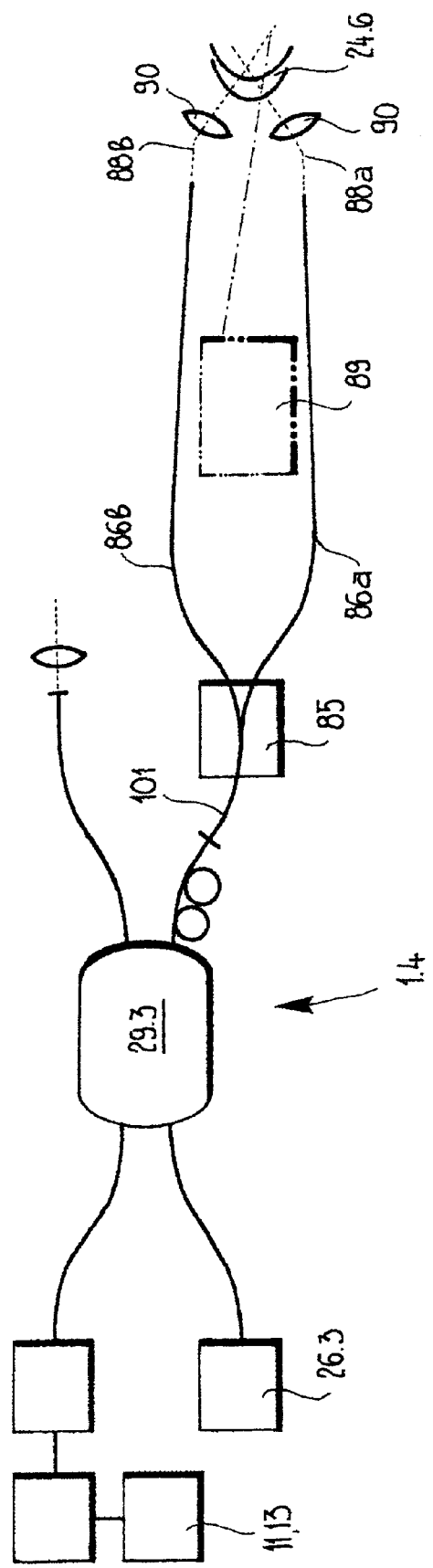
FIG. 9 shows a variant design that permits a peripheral cornea thickness measurement or sclera thickness measurement.

FIG. 9 shows a further design variant. A peripheral corona thickness measurement or sclera thickness measurement is undertaken here. The measuring beam and the therapeutic beam now no longer run with one another. By contrast with the apparatus 1.1 sketched in FIG. 2, here the measuring radiation is split up with the aid of a fiber coupler 85 into a plurality of component radiations, the component radiations in radiation conductors 86a, 86b, . . . being arranged with a preferably annular arrangement around a beam 87 of a therapeutic laser 89. Peripheral cornea thickness measurements can be undertaken with this arrangement. For the sake of clarity, only two component beams 88a and 88b emerging from the two radiation conductors 86a and 86b are drawn in FIG. 9. The measuring beams 88a, 88b, . . . emerging from the fibers are focused by an optical system 90 onto the cornea 24.6 or the sclera. The diameter of the annular arrangement can be varied manually or in an automated fashion such that the cornea thickness can be measured at various concentric rings of different diameter. The interference signal is detected here with the aid of a detector 94 and processed with the aid of a signal processing unit 50.3.

A selection of different measuring sites can be achieved by an appropriate design of the fiber coupler 85. This fiber coupler 85 can be designed, for example, as a fiber optic switch that switches the radiation over in a short time sequence from one radiation conductor into another radiation conductor. The interference signals of various measuring sites are therefore separated temporally from one another and can therefore be assigned to the measuring site. The switching times are typically in the millisecond region.

A wavelength-selective fiber coupler can also be used instead of the abovementioned fiber coupler 85. In this case, a broadband radiation from the radiation source 26.3 is split up into a plurality of radiation conductors in the frequency domain. The radiations guided in the individual radiation conductors should as far as possible not overlap in the frequency domain. A further wavelength-selective fiber coupler (not illustrated) that guides the radiation onto a number of detectors corresponding to the partial frequencies is then used at the detector end. A detector is then assigned to each measuring site.

Figure 10:
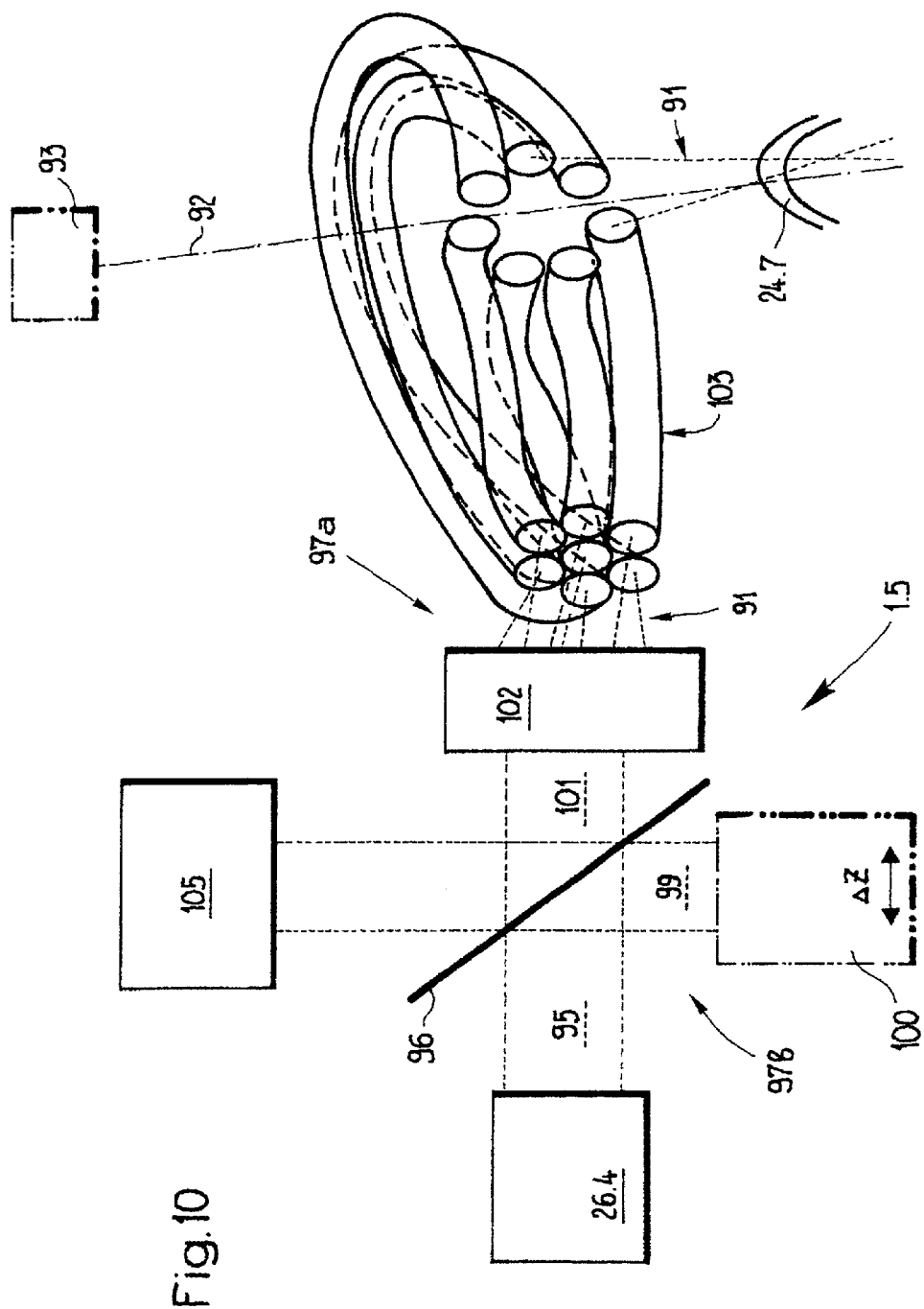
FIG. 10 shows a variant of the embodiment illustrated in FIG. 9.

FIG. 10 likewise shows an exemplary embodiment relating to peripheral cornea thickness measurement or sclera thickness measurement, here, as well, a bundle of measuring beams 91 not being coupled into the beam path 92 of a therapeutic laser 93. By analogy with the design in FIG. 9, here, as well, a measuring radiation 95 coming from a radiation source 26.4 is split up with the aid of a beam splitter 96 into a measuring arm and a reference arm 97a and 97b. As already mentioned above, a reference radiation 99 is guided in the reference arm 97b to a wavelength variator 100, subjected to optical wavelength variation and retroreflected. A measuring radiation 101 is split up in the measuring arm 97a with a collimator array 102 into a plurality of measuring beams 91, each component beam then being coupled into a conductor or a conductor bundle 103. The conductors of the bundle 103 are arranged in a prescribed configuration in front of a cornea 24.7 to be measured. The conductors can be of annular configuration. The radiation reflected by the front and rear sides of the cornea 24.7 passes again into the individual conductors of the bundle 103 and is shaped by the collimator array 102 into a "free-space radiation" that interferes with the radiation reflected by the wavelength variator. The interfering radiation is detected with the aid of a one-dimensional or two-dimensional detector array 105 and processed by analogy with the statements made above with the aid of a parallel amplifier circuit, a parallel filter circuit, possibly a parallel rectifier circuit and possibly a parallel envelope-forming circuit. This entire parallel circuit from photodetection up to envelope formation can be integrated, for example, on a CMOS chip.

The above-described invention renders it possible for the cornea thickness to be measured in real time at one or more points of the cornea before, during and after the removal of the epithelium, or before, during and after the cutting of a corneal flap. The invention also renders it possible for the cornea thickness to be measured at one or more points of the cornea before, during and after the photorefractive cornea treatment. In addition, the invention can supply the measured data that are required in order to determine the topography of the cornea, the radii of curvature on the cornea surface and the cornea elevation. The device according to the invention can be used for various surgical techniques (PRK, PTK, LASIK, LASEK). The device can be used, on the one hand, to control the therapeutic laser such that a previously prescribed (possibly patient-specific) critical cornea thickness is not undershot during the ablation of the cornea. In the case of what is termed LASIK technique, in particular, this critical residual thickness is undershot. Undershooting this critical residual thickness can lead to severe complications. The subject matter of the invention is preferably equipped with a software and a connection to the therapeutic laser in such a way that the laser intervention can be controlled automatically on the basis of the real-time measurement of the cornea thickness. If necessary, laser parameters can be modified thereby such that a prescribed dioptric change can be carried out nevertheless without undershooting the critical cornea thickness. This is achieved by diminishing the diameter of the ablation zone during treatment, if required. By diminishing the diameter of the ablation zone, the prescribed dioptric change is already achieved at a shallower ablation depth, and so the risk of undershooting the critical cornea thickness KD is banished. For the myopia correction, the connection between dioptric change, diameter of the ablation zone and the central ablation depth is given approximately by the following formula in accordance with Cornea, Volume III, Surgery of the Cornea and Conjunctiva, Jay H. Krachmer, Mark J. Mannis, Edward J. Holland; Mosby, 1997:

$$t_0 = -(S^2 D)/3,$$

$t_0$ denoting the maximum ablation depth on the optical axis in $\mu$m, S the diameter of the ablation zone in mm, and D the dioptric change in dpt. The same formula holds approximately in the case of the hyperopia correction, but $t_0$ in this case denotes the maximum ablation depth in the periphery of the cornea, it being presupposed that no ablation takes place in the center of the cornea. More accurate and more general formulae for the dioptric change as a function of the ablation are likewise to be found in the above-named literature.

The measuring beam can be coupled in at various sites of the device designed as a therapeutic laser unit. The sites with deflection mirrors are to be preferred in this case. Coupling in at these sites is easy, since all that is required is to replace the deflecting mirror by a beam splitter designed accordingly for the wavelengths of the radiations used.

The beam splitter (or splitter mirror) is a component of the optical coupling system 37.1 to 5. In addition to this beam splitter, the optical coupling system 37.1 to 5 consists of a monomode fiber, a fiber plug and a lens (or a lens system). The sequence of these components in the direction from the fiber coupler to the eye is as follows in this case: monomode fiber 35 or 74, fiber plug 36.1b or 77, lens (or lens system), beam splitter (or splitter mirror). The fiber plug and lens (or lens system) in this case form the beam shaping unit 6. The beam shaping unit 6 has the task of shaping the measuring beam such that its beam cross section on the one hand as far as possible does not overshoot the aperture diameter prescribed by the therapeutic device, and on the other hand is focused (in combination with the optical system prescribed by the therapeutic unit) on the cornea.

The use here of two lenses in the beam shaping unit 6 is not mandatory; it is also possible to use scanner mirrors instead of this.

The measuring beam can be coupled in not only at those sites of the therapeutic laser unit at which a deflecting mirror is present. It can also be coupled in the beam path of a video camera or a fixation laser that are both present as a rule in a therapeutic unit. An additional beam splitter is required, however, in this case. This beam splitter then splits either the radiation of the measuring beam or the radiation of the fixation laser. The coating of the required beam splitter is easy to produce, since the wavelength of the measuring beam of 1300 nm differs both strongly from the radiation wavelength of approximately 850 nm normally used for the video camera and strongly from the normally used wavelength of the fixation laser of approximately 650 nm.

The measuring device 1.1 or 1.2 or 1.3 can be used together with a stereomicroscope—with a large working distance of approximately 30 cm, as a rule. The measuring beam of a short coherence reflectometer described above and also in variants below, can now be faded into one of the two beam paths of the stereomicroscope. If, in addition, a video camera is to be provided, it is possible to work with a beam splitter. The fact that the measuring beam no longer impinges perpendicularly on the cornea is a disadvantage of coupling the measuring beam into the beam path of a stereomicroscope. Specifically, the two viewing beams must be inclined relative to one another in order to produce a stereoviewing effect. One measuring beam of the measuring device can also be guided into the optical axis of a stereomicroscope and be guided there, with the aid of a small reflecting mirror (in the center between the two viewing beams) that should disturb the two stereoviewing beam paths as little as possible, through the objective onto a cornea to be treated and/or measured. In this case, the numerical aperture of the stereomicroscope must be large enough to pick up the specularly reflecting measuring radiation. On the other hand, the sensitivity of the photodetectors 40, 47a, 47b or 63a and 63b of the measuring device 1.1, 1.2 or 1.3 must be sufficiently high to detect the measuring radiation carried back into the entire half space.

In the case of a further variant use of the measuring devices 1.1, 1.2 and 1.3 together with a stereomicroscope, the optical axis of the stereomicroscope and the axis of the therapeutic beam path coincide. A beam splitter is then arranged in each stereoviewing path, that is to say outside the therapeutic beam path, for the measuring radiation of the measuring devices 1.1, 1.2 and 1.3. By contrast with the previous design variant, conditions imposed on the numerical aperture of the stereomicroscope, and the sensitivity of the photodetectors are less strict here. If stereoviewing is dispensed with, the individual "stereobeam paths" can be used for different applications. For example, one of the two beam paths can be used for video viewing.

Figure 11:
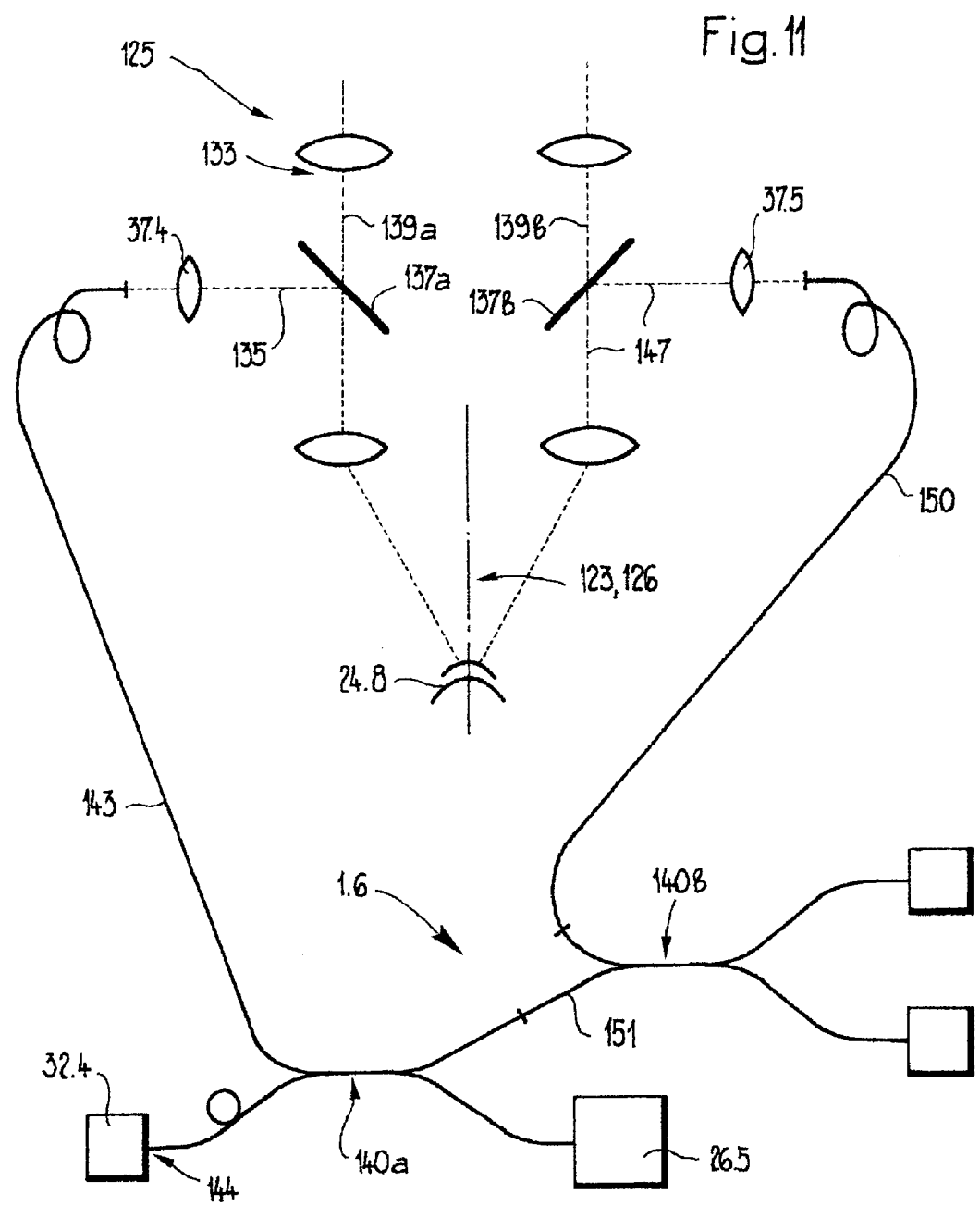
FIG. 11 shows a further variant, with coupling of the measuring radiation into a stereomicroscope.

A further design variant is illustrated in FIG. 11, one measuring device 1.6 here being slightly varied as compared with the measuring devices 1.1, 1.2, 1.3 and 1.4 in FIGS. 2, 3, 4 and 9. The measuring device also co-operates here with a stereomicroscope 133. The free measuring radiation 135 is coupled here, however, into the beam path 139a of the microscope 133 with the aid of a first beam splitter 137a, and coupled out of the other beam path 139b with the aid of a further beam splitter 137b after reflection at the front and rear sides of the cornea 24.8 to be measured. Here, the measuring device 1.6 has two fiber couplers 140a and 140b and two detectors 142a and 142b. As already explained above, the fiber coupler 140a splits up the radiation coming from a radiation source 26.5 into a radiation conductor 143 and into a reference arm 144 with a path length variator 32.4. By analogy with the above-described design variants, the radiation guided in the radiation conductor 143 is shaped with the aid of an outcoupling unit (collimator unit) 37.4 to form the parallel free-space beam 135. The free-space beam 147 reflected by the cornea 24.8 and deflected by the beam splitter 137b is coupled into a radiation conductor 150 with the aid of a coupling unit (collimator unit) 37.5. The radiation conductor 150 is connected to the fiber coupler 140b. The portion of radiation reflected by the wavelength variator 32.4, which is guided to the fiber coupler 140b via a radiation conductor 151 from the fiber coupler 140a then interferes in the fiber coupler 140b with the portion of radiation, coming via the radiation conductor 150, reflected at the cornea 24.8. The optical path length from the fiber coupler 140a via the left-hand and right-hand beam paths 139a and 139b of the microscope 133 up to the fiber coupler 140b must be the same length as that from the fiber coupler 140a to the wavelength variator 32.4 and back to the fiber coupler 140b with a tolerance given by the coherence length of the radiation source 26.5. Interference then occurs in the fiber coupler 140b between the two radiations separated by the fiber coupler 140a, given such a correspondence between the wavelengths. The interference is detected by the two detectors, a single detector also being sufficient when the signal noise component is low.

Irrespective of the site and type of coupling of the measuring radiation into the beam path of a microscope, determined measured values and other information such as the instantaneous residual thickness of the cornea or the distance still missing up to the critical thickness $d_{crit}$ of the cornea can also be coupled in using image technology. These data can be faded into the eyepiece of the microscope as numbers and/or letters and/or different color designations via a beam splitter (not illustrated).

It is also possible to provide a key or a foot pedal in order to determine an instant at which the measured value present at the relevant instant is accentuated, stored with this accentuation in a memory and/or illustrated with this accentuation on a display or a monitor. Particular instants can be, for example:

- the instant immediately before or after fitting a suction ring of a microkeratome.
- the instant immediately before or after cutting a corneal flap,
- the instant immediately before or after scraping away the corneal epithelium,
- the instant immediately before or after rinsing the cornea and/or the sclera,
- the instant immediately before the first or the last laser pulse, or
- the instant immediately before or after folding back a corneal flap.

The measurement explained above can be used to measure a thinning of the cornea and to compare it graphically and computationally with a planned thinning. It is also possible to determine thinning-relevant factors such as, for example, evaporation of water from the cornea and/or thickening-relevant factors such as swellings owing to a surgical operation. The evaporation of water determined per time unit is then used for the purpose of controlling a surgical or therapeutic laser beam in real time. Cornea thickness values that are a function of the air humidity and air temperature will be stored and used during ablation in order to compensate environmental conditions in the operating room. It is also possible to store typical cornea thickness values relating to age, sex and composition of the cornea as well as their temperature response and then call them up for the purpose of relevant treatment.

It was possible, moreover, to determine by means of the above-described method that a patient-independent ablation rate of the cornea is not sufficient for satisfactory results. It is also impossible to assume, as previously customary, that the ablation laser ablates a cornea layer of constant thickness per laser pulse during the entire ablation. A calibration of an ablation rate only once in a prescribed time frame (to date, mostly one day) is therefore insufficient. Moreover, the water content and the thinning of the cornea as a consequence of evaporation of the water contained in the cornea can vary as a function of the patient.

In order to correlate the cornea thickness measurement with the intended ablation of the laser, it is therefore not sufficient only to know the cornea thickness at a prescribed instant. Specifically, for an optimum treatment it is necessary, in addition, also to know the instant when cutting the flap is accomplished, or the instant when scraping of the epithelium is accomplished, and then to know the cornea thinning per time unit as a consequence of evaporation. Again, the cornea thickness can still change after a treatment for various reasons.

The laser ablation pulses can now be controlled automatically on the basis of input empirical values. These empirical values can be a function of, for example, age, sex and case history. The empirical values can, however, also be determined for the present without ablation with the aid of the above-described measuring method.

The above-described cornea thickness measurements can further be supplemented with a distance measurement and/or an "alignment measurement", in order to carry out the desired ablation exactly even when the ablation response of the laser were to be a function of the position of the patient's eye. This influence is negligible or must be taken into account depending on the numerical aperture of the laser beam and the operation technique. The ablation rate can be better controlled if account is taken of a change in distance between a reference point and the patient's cornea. Specifically, each laser beam has a certain divergence which, given a variation in the position of the patient's eye in the direction of propagation of the beam, causes a variation in the beam diameter on the eye.

The numerical aperture of the measuring beam describes a maximum angular tolerance with which the eye (or the cornea) of the patient may deviate from an optimally aligned position without losing the measuring signal. Specifically, if the patient does not fixate exactly on a fixation laser point, the measuring beam no longer strikes the two cornea surfaces perpendicularly. The measuring beam is no longer retroreflected into itself, and no measuring signal can be detected, as a result. Automatic interruption of the cornea ablation then occurs, since ablation errors would otherwise result.

If only one CCD camera were to be used for monitoring, it could only be determined how far the middle of the pupil is removed from the ablation laser axis. In the case of this monitoring method, however, it is also impossible to distinguish between a lateral displacement of the cornea and the defective angular alignment.

The water content of the cornea, which likewise influences the refractive data, can be determined by a measurement using two different measuring wavelengths, one wavelength being, for example, in the range between 450 nm and 1300 nm, and the other wavelength being close to an absorption maximum of water. The absorption maximum of water is at a wavelength of 1800 nm and 400 nm. In the event of cornea thinning as a consequence of water evaporation, the cornea thickness measured by one wavelength changes differently from that of the other wavelength. A conclusion on the water content can be made from these different values.

Figure 12:
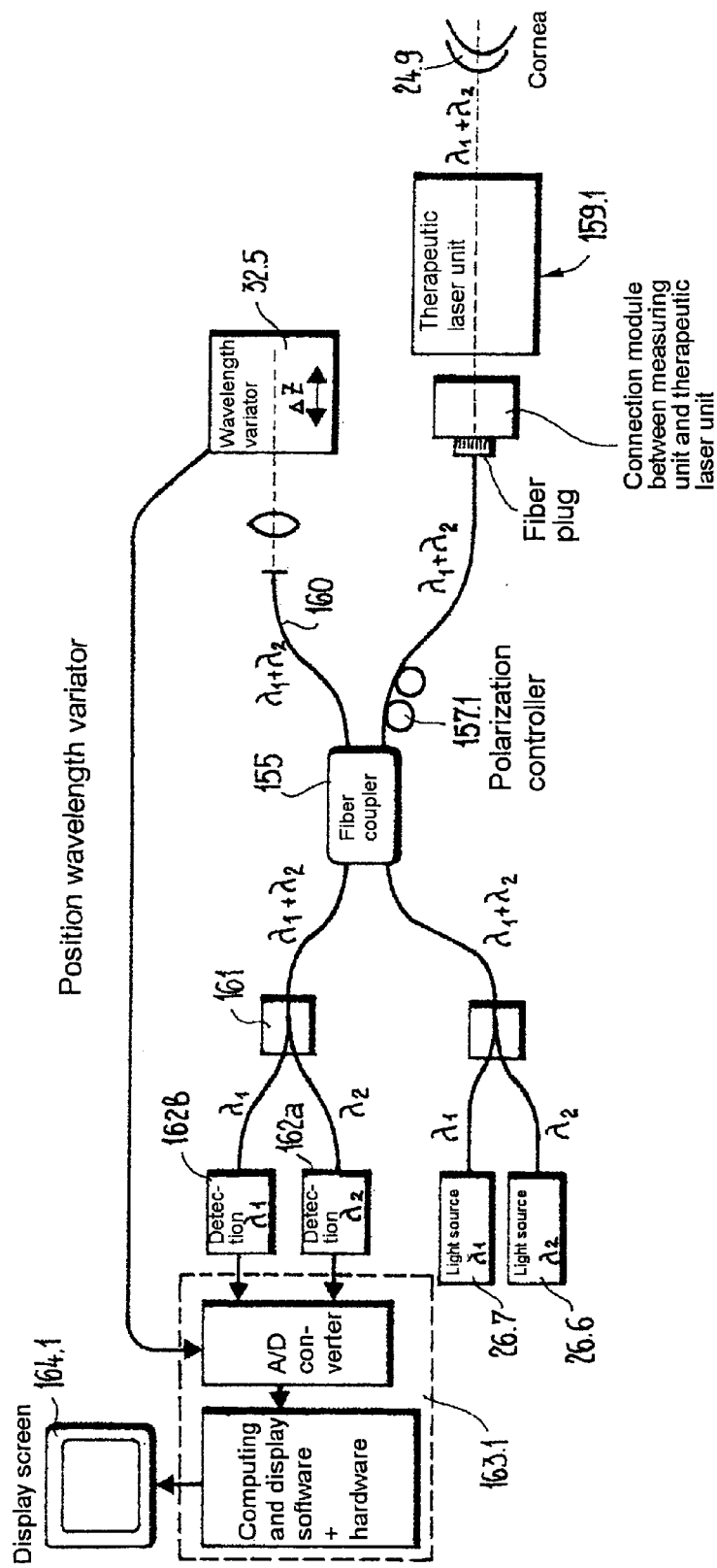
FIG. 12 shows a schematic arrangement for determining the water content in the cornea.
Figure 13:
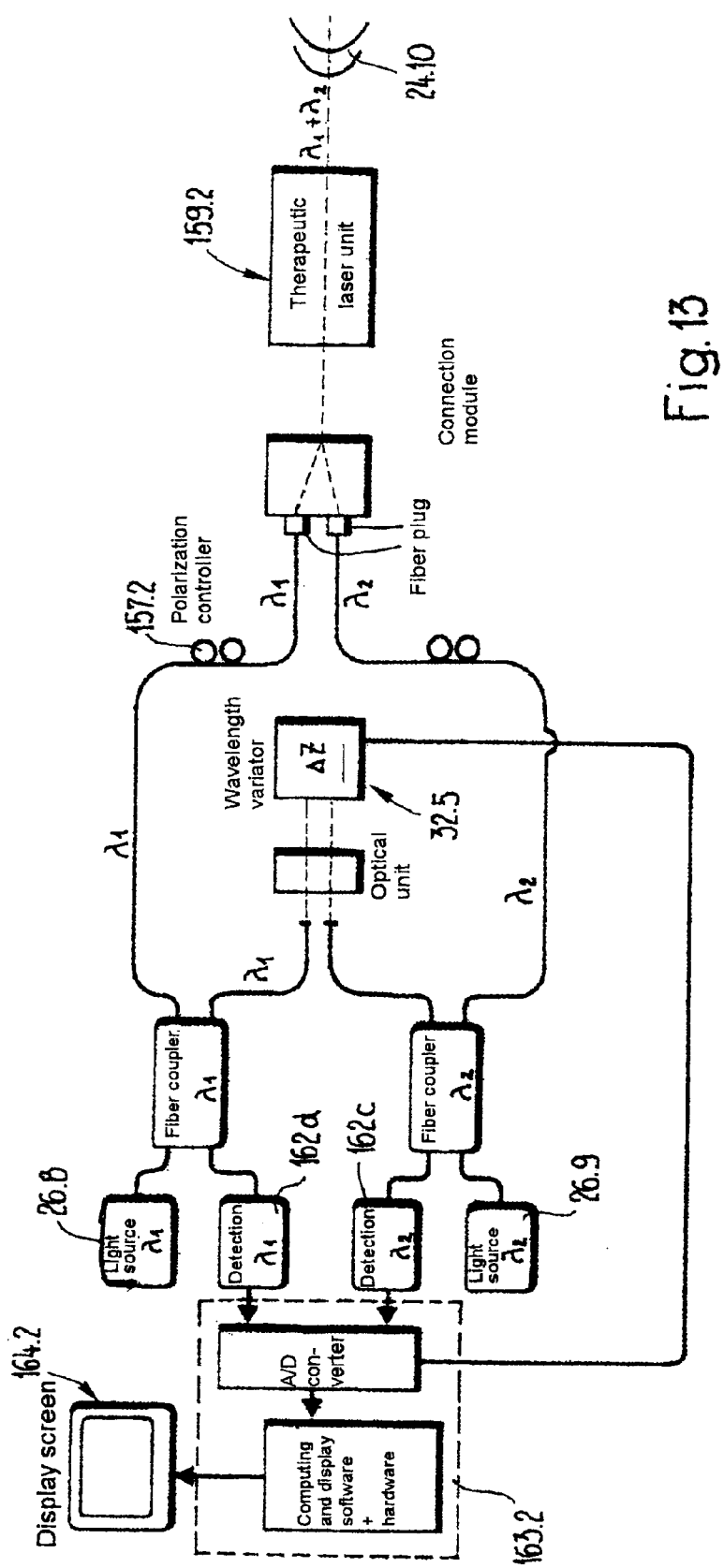
FIG. 13 shows a variant of the arrangement illustrated in FIG. 12.

An arrangement for determining the water content is shown by FIGS. 12 and 13. The design illustrated in FIG. 12 has two radiation sources 26.6 and 26.7, which by analogy with the above statements emit radiations with different wavelengths $\lambda_1$ and $\lambda_2$. The two radiations of different wavelengths are led in a single radiation conductor to a fiber coupler 155. A waveguide 156 leads from the fiber coupler 155 via a polarization controller 157.1 and an optical unit (therapeutic unit) 159.1 to the cornea 24.9. A further radiation conductor 160 leads from the fiber coupler 155 to a path length variator 32.5. The interference signal is led from the fiber coupler 155 via a radiation conductor 161 and a separation into the different wavelengths the two detectors 162a and 162b. The signals of the two detectors 162a and 162b are evaluated in an evaluation circuit 163.1 in order to determine the water content. The respective results can then be illustrated graphically on a display screen 164.1.

A variant arrangement analogous to this is illustrated in FIG. 13. Also, two radiation sources 26.8 and 26.9, are used here, which emit radiations of different wavelengths $\lambda_1$ and $\lambda_2$, two detectors 162c and 162d for the interference signals of different wavelengths $\lambda_1$ and $\lambda_2$, a path length variator 32.5, an optical unit 159.2, an evaluation circuit 163.2, a polarization controller 157.2 and a display screen 164.2 as well as two fiber couplers.

The abovedescribed cornea thickness measuring units and distance measuring units [distance measurement from a reference point to the front side of the cornea] can be integrated to form a novel laser keratome via a beam splitter. Apart from the advantages already set forth above, it is then additionally possible to measure the flap thickness with micrometer accuracy. This laser keratome is used to cut a corneal flap with the aid of short pulses, preferably in the femtosecond region. The cutting of the flap is then followed by the ablation of the cornea already described above.

So far, the flap has been cut mechanically with the aid of what is termed a microkeratome, using a motorized blade. The known microkeratomes had a suction ring with the aid of which they were pressed onto the surface of the eye in order to prevent slippage during the cutting operation. Cutting faults ("free caps", "button holes") frequently occurred in the case of the known methods, and the mechanical contact with the eye produced, in addition, an overpressure in the eye that was undesired even if of short duration. These disadvantages are avoided with the novel laser keratome.

What is claimed is:

1. A device with a first laser radiation source for material ablation of partial ablation regions of a surface of a radiation-transparent or diffusive object having a thickness, said device comprising:
   a control device,
   said first laser radiation source emitting a first laser radiation being controllable by the control device,
   a measuring device having a Michelson interferometer, said Michelson interferomoter having a reference arm, a measuring arm and a second laser radiation source, said second laser radiation source emitting a measuring beam with a center wavelength in a region of 1,310 nm traveling as reference radiation in said reference arm and as measuring radiation in said measuring arm; and
   a monomode fiber for said center wavelength in the measuring arm so that an optical wavelength in air can be compensated acceptably in the measuring arm;
   an electronic evaluation unit being connected by a signal to the control device, said electronic evaluation unit using measured values determined with the measuring device for evaluating a relative distance of said partial ablation region from a reference value together with the thickness of the object, and for evaluating a prescribed thickness profile, and using the evaluated thickness profile to control the first laser radiation source, the latter being released only if the control device has determined a stored distance value lying in a prescribed tolerance range, and/or has determined an inclination of the partial ablation region within stored tolerance values.

2. The device as claimed in claim 1, wherein said measuring arm having a multiple beam with the aid of which the measuring beam can be split up into a plurality of partial measuring beams that can be guided onto the object for the purpose of determining the thickness profile, and the interferometer preferably having a detector, designed as a detector array for the interference between the reference radiation and measuring radiation.

3. The device as claimed in claim 2, wherein the multiple beam divider unit is a collimator array.

4. The device as claimed in claim 2, comprising a fiber bundle with which the plurality of partial measuring beams can be guided onto the object.

5. The device as claimed in claim 1, further comprising a beam deflecting unit for deflecting the measuring beam of the second laser radiation source over a surface of the object, in a linear fashion in order to determine a two-dimensional thickness profile of the object.

6. The device as claimed in claim 5, wherein the beam deflecting unit is an internally aluminized hollow cylinder that the measuring beam of the Michelson interferometer strikes evenly on an outwardly cambered surface, except for an angular tolerance in positions deviating from an optical axis such that a cornea thickness can be measured in as a wide a region as possible around the cornea center, even in the case of patients with poor or diminished fixation capacity and/or an irregular cornea surface.

7. The device as claimed in claim 1, further comprising a beam deflecting unit for deflecting the measuring beam of the second laser radiation source over a surface of the object, in a planar fashion in order to determine a three-dimensional thickness profile of the object or in order to determine a topography of the object.

8. The device as claimed in claim 7, wherein a beam diameter of the laser beam impinging on a cornea can be adjusted for a prescribed diameter of a ablation zone on a cornea surface of the cornea with the beam deflecting unit connected to the control device, wherein an adjustment being a function of a thickness profile determined by the control device and/or a topography of the object determined by the control device, and/or using the control device to adjust the intensity of the first laser beam on the cornea surface in order to achieve a prescribed ablation depth, and the beam diameter on the cornea and an ablation depth being adjusted automatically in real time by the control device during a surgical and/or therapeutic treatment.

9. The device as claimed in claim 12, wherein
   the beam deflecting unit is an internally aluminized hollow cylinder having an outwardly cambered surface and the said object being a cornea of an eye, and
   said measuring beam strikes said outwardly cambered surface of the cornea perpendicularly, except for an angular tolerance, in positions deviating from the an optical axis, such that the thickness of said cornea can preferably be measured in as a wide a region as possible around a center of the cornea, even in cases of patients with poor or diminished fixation capacity and/or irregular cornea surfaces.

10. The device as claimed in claim 7, wherein said first laser radiation source emitting a laser beam having a diameter and an intensity, said object being a cornea of an eye, said device comprising adjusting means for said laser beam and said intensity, the beam deflecting unit is controlled by the control device as a function of a profile of the thickness of the object determined by the control device and/or of the topography of the object, the first laser beam diameter, impinging on the cornea, being adjustable by said adjusting means in such a way that a prescribed diameter of a partial ablation region results on a surface of the cornea, and/or the intensity of the first laser beam on a surface of the cornea can be adjusted in such a way that a prescribed ablation depth can be achieved, wherein the diameter and ablation depth being adjusted automatically in real time during surgical and/or therapeutic treatment.

11. The device as claimed in claim 1, wherein the object is a cornea of an eye.

12. The device as claimed in claim 1, comprising:

at least one beam splitter, a microscope, having at least an observing partial beam path, said path observing the object, and being a component part of said measuring arm, and said at least one beam splitter coupling said partial beam path into the observing partial beam path of said microscope.

13. The device as claimed in claim 12, wherein said microscope is a stereomicroscope for observing at least a partial beam path, said observing partial beam path being a component part of the measuring arm of the measuring device.

14. The device as claimed in claim 1, wherein the object is a cornea of an eye, a beam deflecting unit for deflecting the measuring beam of the second laser radiation source over the object surface, said first laser radiation emitted by said first laser radiation source having a radiation beam with an intensity and a beam diameter, said beam diameter of said radiation beam impinging on the cornea being adjustable for a prescribed diameter of one of said ablation regions on a surface of the cornea, wherein undertaking an adjustment as a function of the thickness profile determined by said control device and/or a topography of the object determined by said control device, and/or using the control device to adjust the intensity of the first laser beam on the cornea surface in order to achieve a prescribed ablation depth, and for the beam diameter on the cornea and the ablation depth, to be adjusted automatically in real time by the control device during a surgical and/or therapeutic treatment.

15. A device with a laser radiation source for material ablation of a surface of a radiation-transparent or diffusive object having a thickness, said device performing a multiplicity of consecutive partial ablation operations by using radiation to get to partial ablation regions, a Michelson interferometer for determining a relative distance of at least one of said partial ablation regions from a reference value together with an actual thickness of the object automatically before and/or after each ablation operation and, only once when a prescribed distance value has been determined within a tolerance, wherein a subsequent partial ablation value is prescribed automatically, in accordance with a value of the thickness respectively determined, in such a way that a predetermined thickness profile, in particular a two-dimensional, preferably a three-dimensional, thickness profile of the object treated by radiation ablation is obtained after an end of ablation, the device having a control device, a laser radiation source emitting said radiation for ablation and being controllable by the control device, a measuring device comprising said Michelson interferometer and an electronic evaluation unit being connected by a signal to the control device, and designed to use measured values determined with an aid of the measuring device for evaluating the relative distance of the partial ablation region from a reference value together with the thickness of the object, and determining from the latter said prescribed thickness profile, and using the determined thickness profile to control the laser radiation source, the laser being released only if the control device has determined a stored distance value lying in a prescribed tolerance range, and/or has determined an inclination of the at least particular ablation region within a stored tolerance values, wherein the measured device with the Michelson interferometer has a measuring beam source with a center wavelength in the region of 1,310 nm, and a monomode fiber for the center wavelength being used in the reference arm such that the optical path length in air in the measuring arm that is required for carrying out the measurement can be acceptably compensated.

* * * * *

UNITED STATES PATENT AND TRADEMARK OFFICE
CERTIFICATE OF CORRECTION

PATENT NO.    : 6,755,819 B1
DATED         : June 29, 2004
INVENTOR(S)   : Rudolf Waelti It is certified that error appears in the above-identified patent and that said Letters Patent is hereby corrected as shown below:

Column 16,
Line 2, change "optical wavelength" to -- optical path length --.
Line 62, change "claim 12" to -- claim 7 --.

Column 18,
Line 47, change "the measured device" to -- the measuring device --.

Signed and Sealed this

Twenty-eighth Day of September, 2004

JON W. DUDAS
*Director of the United States Patent and Trademark Office*